(12) United States Patent
Kurnik (10) Patent No.: US 7,991,561 B2
(45) Date of Patent: *Aug. 2, 2011

(54) CT DETERMINATION BY CLUSTER ANALYSIS WITH VARIABLE CLUSTER ENDPOINT

(75) Inventor: Ronald T. Kurnik, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1391 days.

This patent is subject to a terminal disclaimer.

(21) Appl. No.: 11/423,377

(22) Filed: Jun. 9, 2006

(65) Prior Publication Data
US 2007/0073490 A1    Mar. 29, 2007

Related U.S. Application Data

(63) Continuation-in-part of application No. 11/241,772, filed on Sep. 29, 2005.

(51) Int. Cl.
G06F 19/00 (2011.01)
G01N 33/48 (2006.01)

(52) U.S. Cl. ............................................ 702/19; 702/20
(58) Field of Classification Search ........................ None
See application file for complete search history.

(56) References Cited

U.S. PATENT DOCUMENTS

| | | | |
|---|---|---|---|
| 2003/0175720 A1* | 9/2003 | Bozinov et al. ............ | 435/6 |
| 2005/0130211 A1* | 6/2005 | Shain et al. ................ | 435/6 |
| 2006/0204972 A1 | 9/2006 | Kurnik | |
| 2007/0073489 A1 | 3/2007 | Kurnik | |
| 2007/0143385 A1 | 6/2007 | Kurnik et al. | |
| 2007/0148632 A1 | 6/2007 | Kurnik et al. | |

FOREIGN PATENT DOCUMENTS

| | | | |
|---|---|---|---|
| WO | WO 97/46707 | A2 | 12/1997 |
| WO | WO 97/46707 | A3 | 12/1997 |
| WO | WO 97/46712 | A2 | 12/1997 |
| WO | WO 97/46712 | A3 | 12/1997 |
| WO | WO 97/46714 | A1 | 12/1997 |

OTHER PUBLICATIONS

Klenchin et al., Inhibition of Rhodopsin Kinase by Recoverin, Journal of Biological Chemistry, Jul. 7, 1995, vol. 270, No. 27, pp. 16147-16152.*
Tibhirani et al., Estimating the number of Clusters in a Data Set Via the Gap Statistic, J.R. Statist. Soc. B. 2001, vol. 63, Part 2, pp. 411-423.*
Anderberg, M.R., *Cluster Analysis for Applications*, 1973, Academic Press, Inc.: New York, NY, Table of Contents Only, pp. vii-x.
Anderson, E. et al., "LAPACK Users' Guide," Third Edition, 1999, located at <http://www.netlib.org/lapack/lug/index.html>, last visited on Aug. 4, 2008, 5 pages.
Bieche, I. et al., "Quantitation of *MYC* Gene Expression in Sporadic Breast Tumors With a Real-Time Reverse Transcription-PCR assay," *Cancer Research*, Jun. 15, 1999, vol. 59, pp. 2759-2765.
Everitt, B.S. et al., *Cluster Analysis*, Fourth Edition, 2001, Oxford University Press Inc.,: New York, NY, Table of Contents only, 2 pages.
Gibson, U.E.M. et al., "A Novel Method for Real Time Quantitative RT-PCR," *Genome Research*, 1996, vol. 6, pp. 995-1001.
Hartigan, J.A., *Clustering Algorithms*, Wiley & Sons, Inc.: New York, Table of Contents Only, pp. ix-xiii.
IMSL, Inc., *User's Manual FORTRAN Subroutines for Statistical Analysis, Stat/Library*™ Version 2.0, Sep. 1991, Table of Contents only, 2 pages.
Kaufaman, L. et al., *Finding groups in Data An Introduction to Cluster Analysis*, 1990, John Wiley & Sons, Inc.: New York, NY, Table of Contents only, 4 pages.
Statsoft, Inc., "Cluster Analysis," located at <http://www.statsoft.com/textbook/stcluan.html>, accessed on Aug. 30, 2005, 11 pages.
Tibshirani, R. et al., "Estimating the Number of Clusters in a Data Set Via the Gap Statistic," *J. R. Statist. Soc. B.* 2001, vol. 63, Part 2, pp. 411-423.
Wang, S-S. et al., "Homogeneous Real-Time Detection of Single-Nucleotide Polymorphisms by Strand Displacement Amplification on the BD ProbeTec ET System," *Clinical Chemistry*, 2003, vol. 49, No. 10, pp. 1599-1607.
Weusten, J.J.A.M. et al., "Principles of Quantitation of Viral Loads Using Nucleic Acid Sequence-Based Amplification in Combination With Homogeneous Detection Using Molecular Beacons," *Nucleic Acids Research*, 2002, vol. 30, No. 6, e26, 7 pages.
Wolfram Research, Inc., "Statistics 'ClusterAnalysis,'" printed from the Mathematica Help Browser, 1988-2005, 20 pages.

* cited by examiner

*Primary Examiner* — Jason Sims
(74) *Attorney, Agent, or Firm* — Kilpatrick Townsend & Stockton LLP; Gerald T. Gray (57) ABSTRACT

Systems and methods for determining the cycle threshold (Ct) value in a kinetic PCR amplification curve. The PCR data set may be visualized in a two-dimensional plot of fluorescence intensity (y-axis) vs. cycle number (x-axis). The data set is transformed to produce a partition table of data points with one column including the fluorescence at cycle (n) and a second column including the fluorescence at cycle (n+i), where i is typically 1 or greater. A cluster analysis process is applied to the partition table data set to determine a plurality of clusters in the partition table data set. In one aspect, the clustering process used includes a k-means clustering algorithm, where the number of identified clusters, k, is greater than or equal to three. In another aspect, a Partitioning Around Medoids (PAM) algorithm is used to identify three or more clusters. Using the identified clusters, a linear slope of each of the clusters is determined based on y(n+1) vs. n, and for each cluster, a ratio of the slope of that cluster with the slope of an adjacent cluster is determined. The ratios are then compared. An end point of a cluster having the largest or smallest ratio represents a specific point of interest in the data curve. The data point representing the elbow or Ct value of the PCR curve is identified as an end point of one of the identified clusters, and the cycle number corresponding to this data point is returned or displayed.

30 Claims, 11 Drawing Sheets

CT DETERMINATION BY CLUSTER ANALYSIS WITH VARIABLE CLUSTER ENDPOINT

CROSS-REFERENCES TO RELATED APPLICATIONS

This application is a continuation-in-part (CIP) of the U.S. application Ser. No. 11/241,772, filed Sep. 29, 2005, entitled "SYSTEMS AND METHODS FOR DETERMINING REAL-TIME PCR CYCLE THRESHOLDS USING A CLUSTER ANALYSIS," which is hereby incorporated by reference in its entirety.

BACKGROUND OF THE INVENTION

The present invention relates generally to systems and methods for processing data representing sigmoid type curves or growth curves, and more particularly to systems and methods for determining characteristic cycle threshold (Ct) or elbow values in real-time PCR amplification curves.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in real-time PCR, or kinetic PCR, to facilitate detection and quantification of the amplification process.

Figure 1:
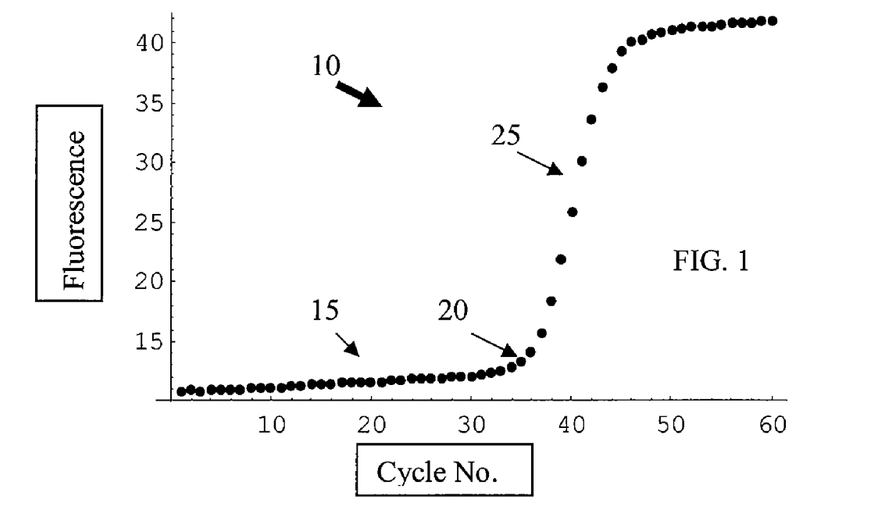
FIG. 1 illustrates an example of a typical PCR growth curve, plotted as fluorescence intensity vs. cycle number.

A typical kinetic PCR curve is shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of quenched fluorescently labeled hybridization probes which only emit fluorescence signals after they are bound to a target nucleic acid sequence and subsequently degraded by the 5' to 3' nuclease activity of a DNA polymerase. Other examples include fluorescent signals generated during nucleic acid amplification where fluorescent dyes bind to double-stranded DNA and experience an increase in their fluorescence quantum yield.

For a typical kinetic PCR growth curve, identifying a transition point referred to commonly as the elbow value or cycle threshold (Ct) value is extremely useful for understanding characteristics of the PCR amplification process. The Ct value may be used as a measure of efficiency of the PCR process. For example, a defined signal threshold is determined for all reactions to be analyzed. Then the number of cycles (Ct) required to reach this signal threshold is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). An elbow value of roughly 35 is shown in FIG. 1 by label 20.

A more precise elbow value in a kinetic PCR curve can be determined using several existing methods. For example, various methods determine the actual value of the elbow (Ct) as the value where the fluorescence reaches a predetermined signal level called the AFL (arbitrary fluorescence value). Other methods use the cycle number where the second derivative of fluorescence vs. cycle number reaches a maximum. All of these methods have drawbacks. For example, derivative methods are sensitive to outlier (noisy) data, and the AFL approach is sensitive to changes in the average baseline fluorescent level in the pre-elbow PCR cycles. Normalization of the data may also provide additional problems. Furthermore, these algorithms typically have many parameters that are often difficult to optimize. This results in a trade-off between sensitivity and false positives that reduces the effectiveness of these algorithm approaches.

Therefore, it is desirable to provide new systems and methods for determining the elbow value in curves, such as sigmoid-type curves, and kinetic PCR curves in particular, that overcome these drawbacks and others.

BRIEF SUMMARY OF THE INVENTION

The present invention provides novel, efficient methods for determining characteristic transition values such as elbow values on sigmoid or growth-type curves. In one implementation, the methods of the present invention are particularly useful for determining the cycle threshold (Ct) value in a kinetic PCR amplification curve.

According to the present invention, a method for determining the elbow or Ct value in a kinetic PCR amplification curve data set is provided. The PCR data set may be visualized in a two-dimensional plot of fluorescence intensity (y-axis) vs. cycle number (x-axis). The data set is transformed to produce a partition table of data points with one column including the fluorescence at cycle n, y(n), and a second column including the fluorescence at cycle (n+i), y(n+i), where i is typically 1 or greater. A cluster analysis process is applied to the partition table data set to determine a plurality of clusters in the partition table data set. Cluster analysis is an analysis tool with a goal of sorting different objects, e.g., data points or vectors, into groups such that the degree of association between any two objects is maximal if the belong to the same group and minimal otherwise. In one aspect, the clustering process used includes a k-means clustering algorithm, where the number of identified clusters, k, is an integer value greater than or equal to three. In another aspect, a Partitioning Around Medoids (PAM) algorithm is used to identify three or more clusters. Using the identified clusters, a linear slope of each of the clusters is determined. For example, the slope of a cluster is determined based on y(n+1) vs. n for the points in the cluster. For each cluster, a ratio of the slope of that cluster with the slope of an adjacent cluster is determined. The ratios are then compared. An end point of a cluster having the largest or smallest ratio represents a specific point of interest in the data curve. The data point representing the elbow or Ct value of the PCR curve is identified as an end point of one of the identified clusters, and the cycle number corresponding to this data point is returned or displayed.

According to an aspect of the present invention, a computer-implemented method is provided for determining a specific point of interest in a region of a curve. The method typically includes receiving a data set representing a curve, the data set including a plurality of first data points each having a pair of coordinate values (x,y), wherein if viewed in a two-dimensional coordinate system the data set includes a region of interest. The method also typically includes applying a transformation to at least a portion of the data set including the region of interest to produce a transformed data set, wherein the transformed data set includes a plurality of second data points, each second data point having a pair of coordinate values (y',y*), where the y' coordinate value of a second data point is the y coordinate value of a corresponding first data point, and the y* coordinate value of the second data point is the y coordinate value of a subsequent first data point. The method further typically includes identifying a plurality of clusters of second data points in the transformed data set, determining a linear slope of each of the clusters, and determining, for each cluster, a ratio of the slope of that cluster with the slope of an adjacent cluster, and comparing the ratios. An end point of a cluster having the largest or smallest ratio represents a specific point of interest in the data curve. In one aspect, the adjacent cluster is a subsequent cluster, and an end point of the cluster having the smallest ratio represents the specific point of interest. In another aspect, the adjacent cluster is a previous cluster, and an end point of the cluster having the largest ratio represents the specific point of interest. In one aspect, the curve is an amplification curve for a kinetic Polymerase Chain Reaction (PCR) process, and the specific point of interest represents the elbow or cycle threshold (Ct) value for the kinetic PCR curve. The coordinate(s) of the identified data point may be returned or displayed. In one aspect, identifying a plurality of clusters includes applying a clustering algorithm, such as a k-means clustering algorithm with k≧3, to the transformed data set. In another aspect, a Partitioning Around Medoids (PAM) algorithm is used to identify three or more clusters.

According to another aspect of the present invention, a computer readable medium is provided that includes code for controlling a processor to determine a cycle threshold (Ct) value in a kinetic PCR amplification curve. The code typically includes instructions to receive a data set representing a kinetic PCR amplification curve, the data set including a plurality of first data points each having a pair of coordinate values (x,y), wherein the data set includes data points in a region of interest which includes the Ct value. The code also typically includes instructions to apply a transformation to at least the portion of the data set including the region of interest to produce a transformed data set, wherein the transformed data set includes a plurality of second data points, each second data point having a pair of coordinate values (y',y*), where the y' coordinate value of a second data point is the y coordinate value of a corresponding first data point, and the y* coordinate value of the second data point is the y coordinate value of a subsequent first data point. The code also typically includes instructions to identify a plurality of clusters of second data points in the transformed data set, to determine a linear slope of each of said clusters, to determine, for each cluster, a ratio of the slope of that cluster with the slope of an adjacent cluster, and to compare the ratios. An end point of a cluster having the largest or smallest ratio represents the Ct value in a PCR amplification curve. In one aspect, the adjacent cluster is a subsequent cluster, and an end point of the cluster having the smallest ratio represents the specific point of interest. In another aspect, the adjacent cluster is a previous cluster, and an end point of the cluster having the largest ratio represents the specific point of interest. In one aspect, the instructions to identify a plurality of clusters include instructions to apply a clustering algorithm, such as a k-means clustering algorithm with k≧3, to the transformed data set. In another aspect, a Partitioning Around Medoids (PAM) algorithm is used to identify three or more clusters.

According to yet another aspect of the present invention, a kinetic PCR system is provided. The system typically includes a PCR analysis module that generates a PCR data set representing a kinetic PCR amplification curve, the data set including a plurality of first data points each having a pair of coordinate values (x,y), wherein the data set includes data points in a region of interest which includes a cycle threshold (Ct) value. The system also typically includes an intelligence module adapted to process the PCR data set to determine the Ct value by applying a transformation to at least the portion of the PCR data set including the region of interest to produce a transformed data set, wherein the transformed data set includes a plurality of second data points, each second data point having a pair of coordinate values (y',y*), where the y' coordinate value of a second data point is the y coordinate value of a corresponding first data point, and the y* coordinate value of the second data point is the y coordinate value of a subsequent first data point. The intelligence module is also typically adapted to identify a plurality of clusters of second data points in the transformed data set, to determine a linear slope of each of said clusters, to determine, for each cluster, a ratio of the slope of that cluster with the slope of an adjacent cluster, and to compare the ratios. An end point of a cluster having the largest or smallest ratio represents the Ct value in the PCR amplification curve. The intelligence module may include a processor in a computer system connected to or separate from the kinetic PCR analysis module, or it may include a processor directly coupled to the kinetic PCR analysis module, e.g., both components may comprise a kinetic PCR thermocycler. In one aspect, the adjacent cluster is a subsequent cluster, and an end point of the cluster having the smallest ratio represents the specific point of interest. In another aspect, the adjacent cluster is a previous cluster, and an end point of the cluster having the largest ratio represents the specific point of interest. In one aspect, identifying a plurality of clusters includes applying a clustering algorithm, such as a k-means clustering algorithm with k≧3, to the transformed data set. In another aspect, a Partitioning Around Medoids (PAM) algorithm is used to identify three or more clusters.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 12b shows a graph of Ct versus baseline slope for the curves of FIG. 12a.

DETAILED DESCRIPTION OF THE INVENTION

General Overview

The present invention provides systems and methods for determining a transition value in a sigmoid or growth curve, such as the end of the baseline region or the elbow value or Ct value of a kinetic PCR amplification curve. The systems and methods of the present invention also provide an indication as to whether a data signal is a noise signal. In certain aspects, a cluster analysis algorithm is applied to the data signal to identify a plurality of data clusters in the signal. An end point of one of the clusters represents the Ct value; the systems and methods provide robust techniques for identifying the specific cluster of which the end point represents the Ct value. The Ct value is then returned and may be displayed or otherwise used for further processing. In certain aspects, a double sigmoid function with parameters determined by a Levenberg-Marquardt (LM) regression process is used to find an approximation to the curve. The curve approximation and parameters are used, in certain aspects, to pre-process the data signal, e.g., to normalize the data signal and/or to remove spikes or outlier data points as may be present in the data signal.

One example of an amplification curve 10 in the context of a kinetic PCR process is shown in FIG. 1. As shown, the curve 10 includes a lag phase region 15, and an exponential phase region 25. Such a curve includes a transitionary region of interest 20 linking the lag phase and the exponential phase. Region 20 is commonly referred to as the elbow or elbow region. The elbow region 20 typically defines a transition in the growth or amplification rate of the underlying process, and identifying a specific transition point in region 20 can be useful for analyzing the behavior of the underlying process.

In a typical PCR curve, identifying a transition point referred to as the elbow value or cycle threshold (Ct) value is extremely useful for understanding efficiency characteristics of the PCR process. Other processes that may provide similar sigmoid type curves or growth curves include bacterial processes, enzymatic processes and binding processes. In bacterial growth curves, for example, the transition point of interest has been referred to as the time in lag phase, $\lambda$. Thus, although the remainder of this document will discuss the invention in terms of its applicability to PCR curves, it should be appreciated that the present invention may be applied to data curves related to other processes.

Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System", *Clin Chem* 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons", *Nucleic Acids Research*, 2002 30(6):26, respectively, both of which are hereby incorporated by reference.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, as shown in FIG. 1, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

Cluster Analysis Processes and Variations

Figure 2:
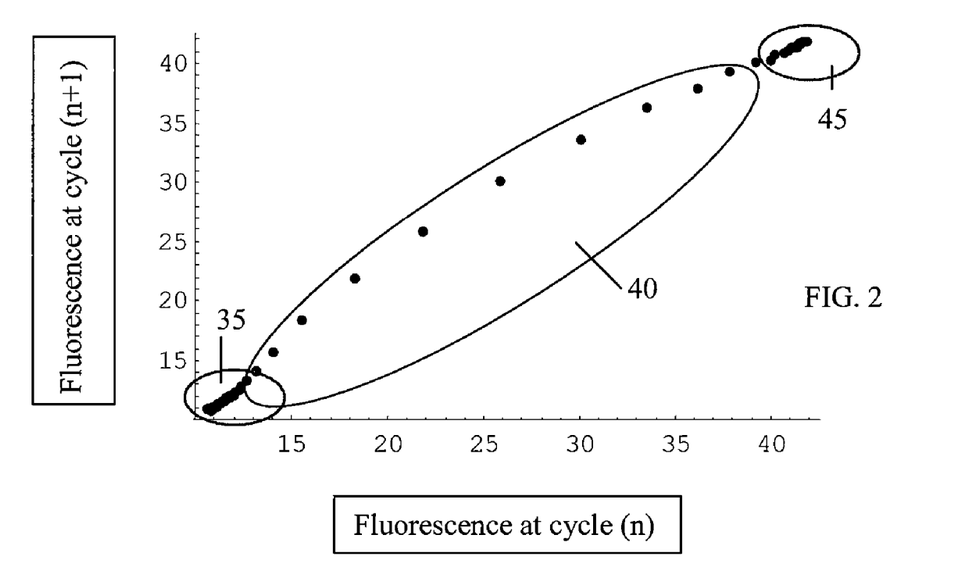
FIG. 2 shows an example of the typical PCR growth curve of FIG. 1, plotted as fluorescence intensity at cycle (n+1) vs. fluorescence intensity at cycle (n).

According to the present invention, one embodiment of a process for determining a transitionary value in a sigmoid type curve, such as the elbow value or Ct value of a kinetic PCR amplification curve, can be described briefly as follows. Typically, PCR data is plotted as shown in FIG. 1, where the fluorescence is plotted vs. cycle number. Although this display gives important information, it does not give information as to how close sequential points are from one another. If instead, the fluorescence at cycle (n+1) is plotted vs. the fluorescence at cycle (n), one obtains the graph shown in FIG. 2. When data are plotted in this manner, it is apparent that the are clusters of data. Three clusters are indicated by the different labeled regions: region 35 at the low fluorescence values represents the baseline region; region 45 at the high fluorescence values represents the plateau region; and region 40 represents the exponential region. As will be apparent, the data may also be represented by additional clusters to give more precise cutoffs of various regions represented by the data. These clusters can advantageously be used to identify the Ct value of the PCR amplification curve. In certain aspects, 5 clusters are determined.

Figure 3:
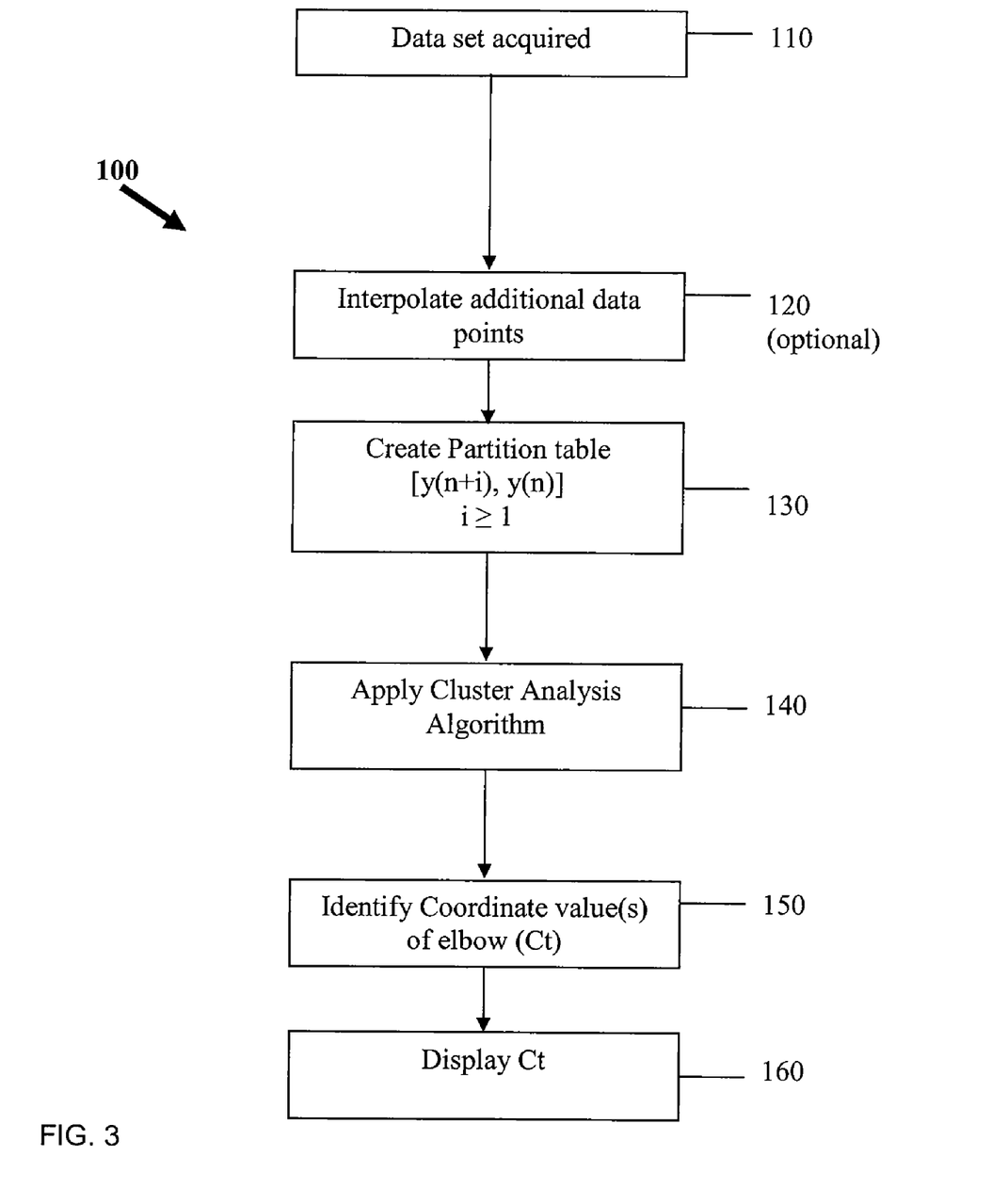
FIG. 3 illustrates a process for determining the elbow value for a PCR process according to one embodiment.

One embodiment of a process 100 for determining the elbow value in a kinetic PCR curve using cluster analysis is shown in FIG. 3. In step 110, the data set is acquired. In the case where process 100 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector) representing the cycle number and the fluorescence intensity value.

After the data set has been received or acquired in step 110, the data set may be analyzed using cluster analysis. Depending on the number of data points acquired in the data set, it may be desirable to increase the number of data points to improve the resolution of the Ct value determined by process 100. Therefore, in one embodiment, additional data points are determined by interpolating between existing data points in step 120. In step 120, a function such as linear interpolation function, a cubic spline function or a least squares fit function is fit to the data points. This may be done using the software application Mathematica® or other application. For example, in one aspect, data points are interpolated between existing data points at cycle number intervals of 1.0 or less, e.g., 0.05 or 0.01, e.g. using a linear interpolation function, or using the cubic spline function or the least squares fit function. In one aspect, a Levenberg-Marquardt regression process is used to interpolate data values. More particularly, a fit function such as a double sigmoid function with parameters determined by Levenberg-Marquardt regression process is used to find an approximation to the data curve. Once the curve approximation has been determined, data values may be interpolated at the desired interpolation scale. U.S. application Ser. No. 11/316,315, filed Dec. 20, 2005, entitled "Levenberg-Marquardt Outlier Spike Removal Method," and U.S. application Ser. No. 11/349,550, filed Feb. 6, 2006, entitled "PCR Elbow Determination by Use of a Double Sigmoid Function Curve Fit with the Levenberg-Marquardt Algorithm and Normalization," each of which is hereby incorporated by reference in its entirety, disclose useful systems and methods for determining curve approximations and fit parameters using a Levenberg-Marquardt regression process.

Figure 4A:
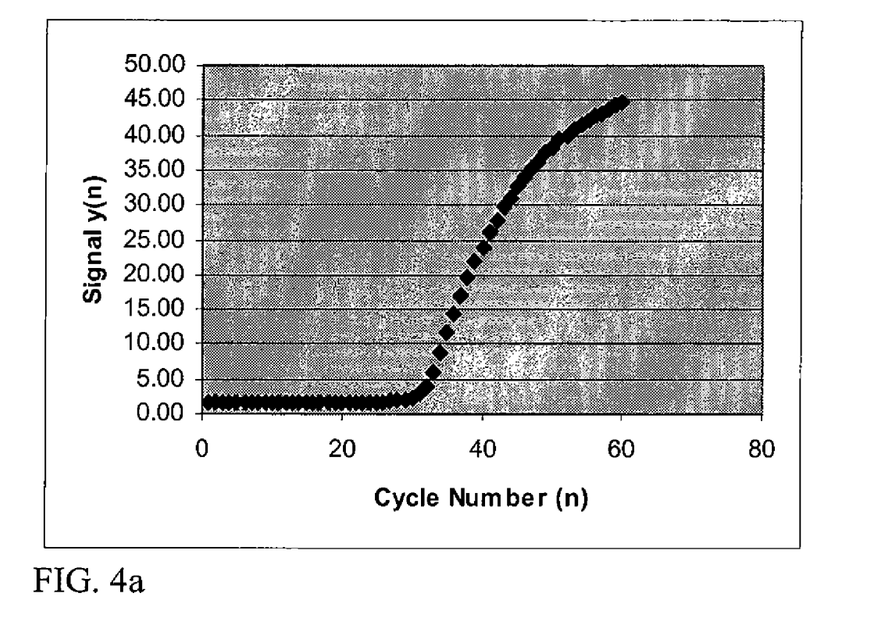
FIG. 4a shows a representation of a data set for an amplification curve and FIG. 4b shows a representation of a corresponding partition table data according to the cluster analysis methods of the present invention.
Figure 4B:
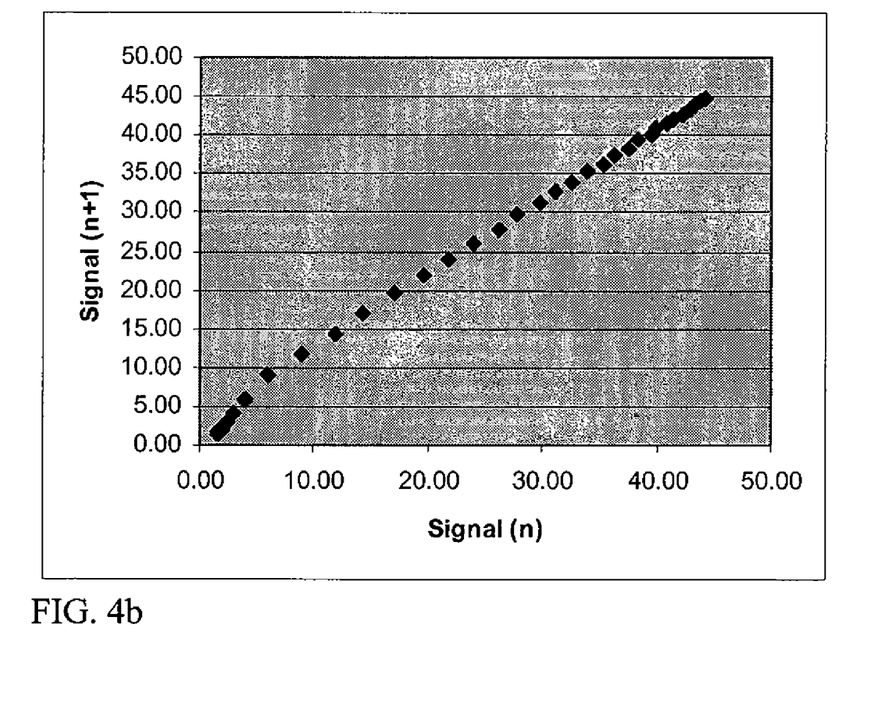
Figure 5A:
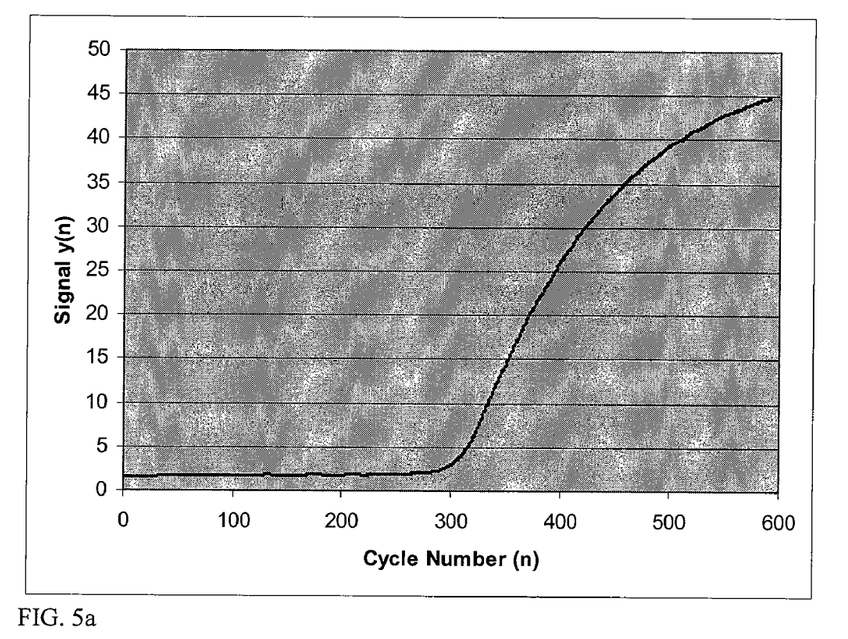
FIG. 5a shows a representation of the data set of FIG. 4a with interpolated data points.
Figure 5B:
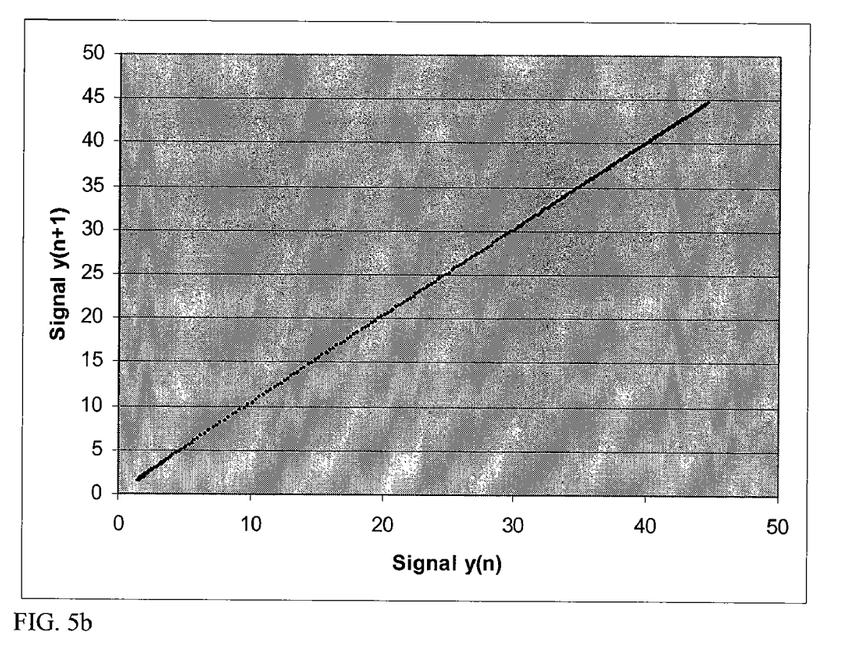
FIG. 5b shows a representation of a corresponding partition table data according to the cluster analysis methods of the present invention.

In step 120, the interpolated data points are also stored along with the actual data points to form a larger table or matrix of data points (x,y) representing cycle number and fluorescence intensity. FIG. 4 shows an example of a data set for an amplification curve, and FIG. 5 shows an example of the data set for FIG. 4 with data interpolated at 0.1 increments. This data set (or the initially acquired data set where no interpolation is performed), or a portion thereof, is then processed in step 130 to produce a set of data points having coordinates (y',y*), where the y' coordinate value is the y coordinate value of a corresponding data point in the table, and where the y* coordinate value is the y coordinate value of a subsequent data point from the table. In Mathematica, for example, this may be performed using the Partition function to create a partition table. In one aspect, the subsequent point is the immediately subsequent data point in the contiguous series of data points, such that a partition table with vector values representing the fluorescence at cycle (n+1) and the fluorescence at cycle (n) is created. FIGS. 4 and 5 show examples of an un-interpolated data set and an interpolated data set, respectively, and a corresponding partition table for these data sets transformed in this manner such that each vector represents [y(n), y(n+1)], where y is cycle number. The data for FIGS. 4 and 5 can be found in Appendix A and Appendix B, respectively of U.S. application Ser. No. 11/241,772, filed Sep. 29, 2005, which is incorporated by reference in its entirety. In another aspect, a subsequent data point includes a data point that is not immediately subsequent to the corresponding data point, such that a partition table with vector values [y(n), y(n+i)] is created, with $i \geq 2$. In general, a partition table with vector values [y(n), y(n+i)], where $i \geq 1$, is created in step 130.

Returning to FIG. 3, in step 140, a cluster analysis algorithm is applied to the partition table to identify a plurality of clusters in the partition table data set. In certain aspects, a clustering algorithm is applied to the partition table to identify 3 or more clusters of data. For example, in one aspect, a k-means clustering algorithm is applied to the partition table, where k is greater than or equal to 3. In another aspect, a Partitioning Around Medoids (PAM) algorithm is applied to the partition table to identify or determine 3 or more clusters. In step 150, the Ct value of the amplification curve is identified. In one aspect, the Ct value is identified as the beginning point or end point in a cluster identified in step 140. For PCR amplification data, in one aspect, it is advantageous to determine 5 clusters of data (e.g., k=5) in the partition table data set. In this case, the Ct value is identified by the last data point in the first cluster (e.g., the cluster with the smallest fluorescence values). In one aspect, if interpolated data is used from step 120, the Ct value is identified by dividing the last value in the first cluster by (1/increment value)+0.9. For example, if the index of the last value of the first cluster equals 352, where interpolation increments of 0.1 cycles were used, the Ct value would be calculated as (352/(1/0.1))+0.9=352/10+0.9=35.2+0.9=36.1. It should be appreciated that the calculation could be altered such that a number other than 0.9 is added (or subtracted). In step 160, the Ct value is displayed, e.g., on a monitor, or printout, LCD screen, etc., or otherwise provided to an operator of the system. It should be appreciated that the Ct value may be obtained by using a point in the cluster other than an end point, for example, the point next to the end point (e.g., endpoint −1), two points away from the end point (e.g., endpoint −2), etc., may be used. When interpolation (step 120) is used to provide additional data points, one could use the endpoint −1, −2, etc. and obtain a "sufficiently accurate" Ct value, provided the interpolation increment is small enough. For instance, if one interpolated in 0.01 increments, and used the endpoint −1, then the Ct would "be off" by 0.01, which is fairly insignificant.

Figure 6:
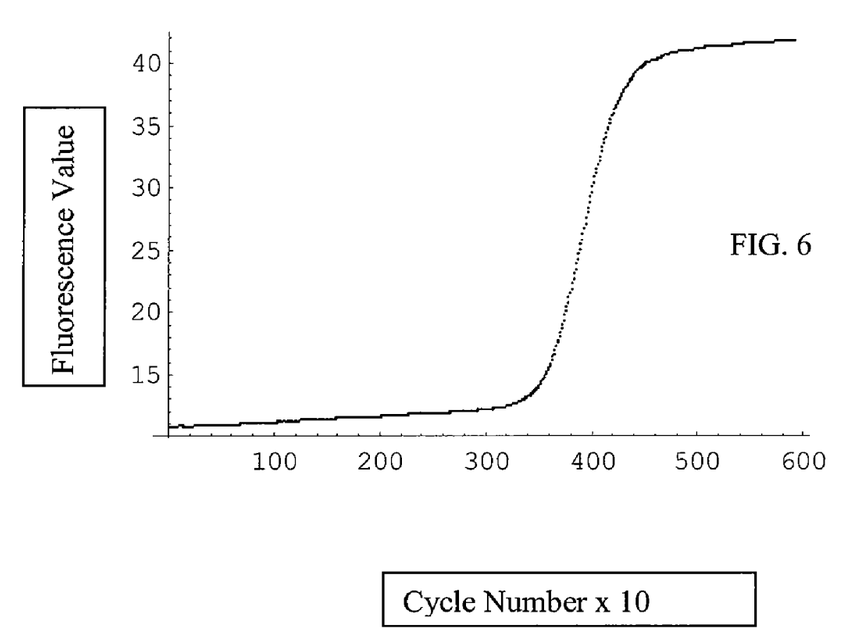
FIG. 6 shows the data of FIG. 1 with linear interpolation at 0.1 increments, thus the cycle numbers are multiplied by 10.
Figure 7:
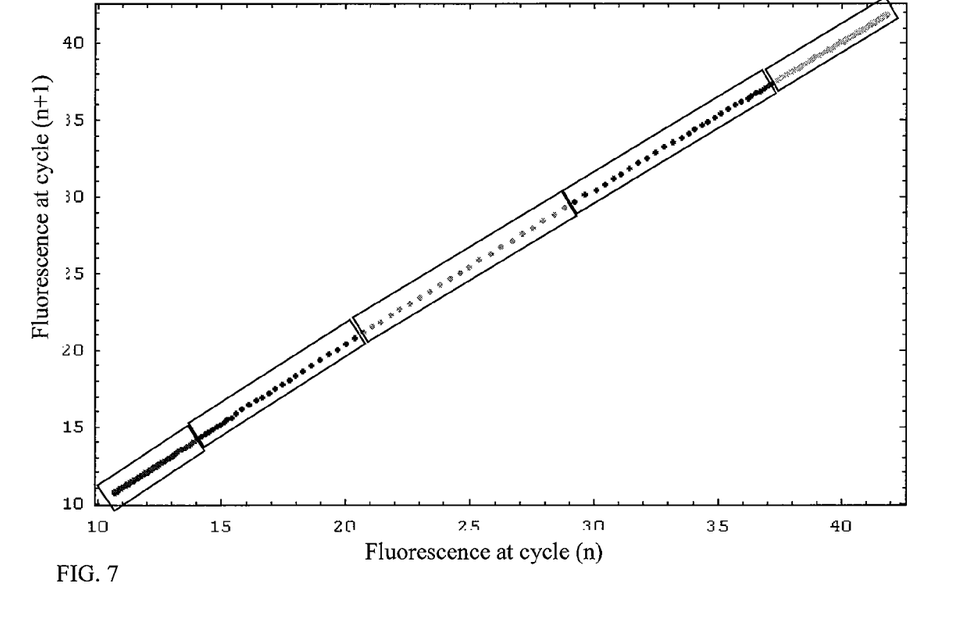
FIG. 7 shows the fluorescence values of the interpolated data of FIG. 6 plotted, with the x-value representing the fluorescence at cycle (n) and the y-value representing the fluorescence at cycle (n+1). The five clusters are indicated by the different colored boxes.

FIGS. 6 and 7 illustrate an example of process 100 applied to the data set of FIG. 1. FIG. 6 shows the data of FIG. 1 with linear interpolation at 0.1 increments, thus the cycle numbers are multiplied by 10. FIG. 7 shows the fluorescence values of the interpolated data of FIG. 6 plotted, with the x-value representing the fluorescence at cycle (n) and the y-value representing the fluorescence at cycle (n+1). The five clusters are indicated by the different colors. The Ct value for this data, using process 100, was determined to be Ct=35.9.

It should be appreciated that the Ct determination process 100, or portions thereof, may be implemented in computer code running on a processor of a computer system. The code includes instructions for controlling a processor to implement various aspects and steps of the determination process 100. The code is typically stored on a hard disk, RAM or portable medium such as a CD, DVD, etc. Similarly, the process 100, or portions thereof, may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

An example of Mathematica code configured to perform the operations of process 100 on a vector yd of fluorescence values is shown below:

```
ClustMod[yd_] :=Module[{ },
    IntF = Interpolation[yd, InterpolationOrder → 1];
    IntTable = Table[IntF[x], {x, 1, Length[yd], 0.1}];
    ParYd = Partition[IntTable, 2, 1];
    fc = FindClusters[ParYd -> Range[Length[ParYd]], 5];
    N[Last[fc[[1]]] /10] + 0.9]
```

In addition to a k-means clustering algorithm, one skilled in the art will understand that other clustering algorithms may be used. Generally, cluster analysis includes a variety of algorithm types, each with a goal of sorting different objects, e.g., data points or vectors, into groups such that the degree of association between any two objects is maximal if the belong to the same group and minimal otherwise. A clustering algorithm places objects into clusters according to defined similarity rules, such as a distance measure (e.g., Euclidian distance). K-means clustering, where the number of cluster groups obtained is decided a-priori, is but one variety of known clustering algorithms. Another type of clustering algorithm, know as Partitioning Around Medoids (PAM), finds the data points (medoids) about which the remaining data are clustered; the user can specify the number of clusters or allow the algorithm to determine how many clusters are present. Yet another type of clustering algorithm, Agglomerative Hierarchical Clustering (AHC), uses an agglomerative hierarchical method starting with each member of the set in a cluster of its own and fusing nearest clusters until there are k remaining. Other types of clustering algorithms include joining or tree clustering algorithms and expectation maximization clustering algorithms. Additional information on these and other clustering algorithms as would be understood by one skilled in the art can be found in "Cluster Analysis, 4th Edition", by Brain S. Everitt, Sabine Landau, and Morven Leese, Arnold publishers, London, 2001, which is hereby incorporated by reference.

The cluster analysis processes disclosed herein are particularly useful for analyzing PCR growth curves where the assay produced a significant increase in fluorescent signal over that of the baseline. Although this is the general case, there may be situations where the increase in signal is minimal, e.g., where the assay is a slow grower; the intensity signal does not substantially increase over the baseline value. In this situation, it may be desirable to have the Ct value determined at a cycle number other than that end the end of the first cluster. According to one embodiment, the linear slope of data points in each of the determined clusters, e.g., clusters 1-5 where 5 clusters are determined, is calculated. For example, the slope of a cluster is determined based on y(n+1) vs. n for the points in the cluster. Thereafter, the ratio of adjacent slopes is calculated, e.g., slope2/slope1, slope3/slope2, slope4/slope3, and slope5/slope4 is calculated. The ratios are next compared and whichever ratio is the largest determines which cluster endpoint is used. For example, if slope2/slope1 is the largest, then the endpoint of cluster 1 is used, whereas if slope3/ slope2 is the largest, the endpoint of cluster 2 is used, etc. Alternately, the ratios may be determined as follows: slope1/ slope2, slope2/slope3, slope3/slope4, and slope4/slope5. In this case whichever ratio is the smallest determines which cluster endpoint is used. For example, if slope1/slope2 is the smallest, then the endpoint of cluster 1 is used, whereas if slope2/slope3 is the smallest, the endpoint of cluster 2 is used, etc.

In addition, it is advantageous to calculate two diagnostic values using information determined using the cluster analysis techniques of the present invention. These values are the relative fluorescent increase (RFI) and absolute fluorescent increase (AFI). According to one embodiment, the RFI and AFI values are determined by calculating the mean fluorescent value of the data in the first and last clusters, e.g., cluster 1 and cluster 5 where 5 clusters are determined. The RFI and AFI are then calculated by:

$RFI$=(mean fluorescence cluster 5)/(mean fluorescence cluster 1)

$AFI$=(mean fluorescence cluster 5)−(mean fluorescence cluster 1)

The assay developer typically uses certain minimum cutoff values of the RFI and AFI to accept or reject the data set.

Noise

According to one embodiment, a process for determining whether the data set (e.g., PCR data set) acquired in step 110 is noisy or shows a trend is provided. Initially, in step 1, the original data set (e.g., with no interpolated data) is partitioned into a partition table with the first column including the fluorescence at cycle (n), and the second column including the fluorescence at cycle (n+1), similar to step 130 of FIG. 3. Next, in step 2, using a cluster analysis algorithm, such as a k-mean cluster algorithm, three or more clusters are determined for this partitioned data set. The result of this analysis are the indices of the original data. Thereafter, in step 3, the determined cluster results are sorted in order of increasing indices, and it is determined whether the results of steps 2 and 3 are identical. If identical, this shows that there is a definite trend in the data; if the results are unequal, the data is substantially pure noise, and a value, e.g., "−1", is returned as the Ct value to indicate that the data is substantially noise data. If the data show a trend, then analysis of the data is continued as described above to determine the Ct value. Otherwise the analysis is stopped and a Ct of "−1" is given.

An example of code for determining trend data vs. noise data is shown in the following Mathematica code:

```
ClustModSM[yd_] :=Module[{ },
    ParYd = Partition[yd, 2, 1];
    fc = FindClusters[ParYd -> Range[Length[ParYd]], 3];
    Last[fc[[1]]]]
ClustModT[yd_] :=Module[{ },
    ClustModSM[yd];
    fcSM = Flatten[fc];
    fcSMSort = Sort[fcSM];
    If[fcSM == fcSMSort, ClustMod[yd], −1]]
```

In certain aspects, it is desirable to identify whether a data set is substantially noise, and not a valid signal. According to one embodiment, several checks may be used to determine the presence of noise.

According to one aspect, one check used to determine the presence of noise includes determining three (or more) clusters without interpolating the fluorescent signal between cycle numbers. A linear regression is then performed on each of these clusters and the correlation coefficient for fluorescent signal vs. cycle number ($R^2$) is calculated for each case. If the correlation coefficient for each $R^2$ is less than 0.1, then an error message is generated.

According to another noise determination process, the cycle number corresponding to the last endpoint of each of the clusters is determined. A check is then done to test whether pt1<pt2<pt3<pt4<pt5 (where pt 1 is the endpoint of the first cluster, pt2 is the endpoint of the second cluster, etc.) If this is not the case, then an error message is generated.

According to another test, a check is made to determine if all of the data points of fluorescent signal vs. cycle number are linear. Thus, according to one aspect, a correlation coefficient ($R^2$) is calculated using all data points. If the value of $R^2 > 0.99$, the data is determined to be linear, and an appropriate error message is generated.

A listing of an example of a Mathematica computer program that implements aspects of the invention (e.g., cluster determination, slope determination, RFI and AFI determination, etc.) is shown below.

```
ClustMod2[yd_] :=Module[{ },
    res = 0;
    ParYd = Partition[yd, 2, 1];
    fc = FindClusters[ParYd -> Range[Length[ParYd]], 3];
    If[Length[fc[[1]]] > 2,
        {regress1 = Regress[yd[[fc[[1]]]], {1, x}, x];
         Rsq1 = RSquared /. regress1;},
        res = -3];
    If[Length[fc[[2]]] > 2,
        {regress2 = Regress[yd[[fc[[2]]]], {1, x}, x];
         Rsq2 = RSquared /. regress2;},
        res = -3];
    If[Length[fc[[3]]] > 2,
        {regress3 = Regress[yd[[fc[[3]]]], {1, x}, x];
         Rsq3 = RSquared /. regress3;},
        res = -3];
    If[Rsq1 < 0.1 && Rsq2 < 0.1 && Rsq3 < 0.1, Noise = 1,
    Noise = 0];
    If[Noise == 1, res = -3];
    data = Table[{i, yd[[i]]}, {i, 6, Length[yd]}];
    regress = Regress[data, {1, x}, x];
    Rsq = RSquared /. regress;
    If[Rsq ≧ 0.99, res = "L"];
    IntF = Interpolation[yd, InterpolationOrder -> 1];
    IntTable = Table[IntF[x], {x, 1, Length[yd], 0.1}];
    ParYd = Partition[IntTable, 2, 1];
    fc = FindClusters[ParYd -> Range[Length[ParYd]], 5];
    pt1 = N[Last[fc[[1]]] /10];
    pt2 = N[Last[fc[[2]]] /10];
    pt3 = N[Last[fc[[3]]] /10];
    pt4 = N[Last[fc[[4]]] /10];
    pt5 = N[Last[fc[[5]]] /10];
    If[pt5 > pt4 > pt3 > pt2 > pt1, pt1 = pt1 * 1, res = -3];
    data1 = IntTable[[fc[[1]]]];
    data2 = IntTable[[fc[[2]]]];
    data3 = IntTable[[fc[[3]]]];
    data4 = IntTable[[fc[[4]]]];
    data5 = IntTable[[fc[[5]]]];
    regdata1 = Regress[data1, {1, x), x];
    regdata2 = Regress[data2, {1, x), x];
    regdata3 = Regress[data3, {1, x), x];
    regdata4 = Regress[data4, {1, x), x];
    regdata5 = Regress[data5, {1, x), x];
    slope1 = (ParameterTable /. regdata1) [[1, 2]][[1]];
    slope2 = (ParameterTable /. regdata2) [[1, 2]][[1]];
    slope3 = (ParameterTable /. regdata3) [[1, 2]][[1]];
    slope4 = (ParameterTable /. regdata4) [[1, 2]][[1]];
    slope5 = (ParameterTable /. regdata5) [[1, 2]][[1]];
    slopeRatio = {slope2/slope1, slope3/slope2, slope4/slope3,
    slope5/slope4};
    MaxRatio = Max[slopeRatio];
    EndPoint = Flatten[Position[slopeRatio, MaxRatio]][[1]];
    RFI = Mean[IntTable[[fc[[5]]]]] /Mean[IntTable[[fc[[1]]]]];
    AFI = Mean[IntTable[[fc[[5]]]]] -Mean[IntTable[[fc[[1]]]]];
```

-continued

```
    If[ (yd[[Length[yd]]] > yd[[1]]) && res ≠ -3 && res != "L",
        {If [EndPoint == 1, res = pt1 + 0.9];
         If [EndPoint == 2, res = pt2 + 0.9];
         If [EndPoint == 3, res = pt3 + 0.9];
         If [EndPoint == 4, res = pt4 + 0.9];}
    ];
```

According to one embodiment, the data set is pre-processed before the cluster analysis processes are applied thereto. Pre-processing may include normalizing the data curve, removing spike points, etc. According to one embodiment, for example, a double sigmoid Levenberg-Marquardt (DSLM) curve fit with subsequent baseline subtraction is performed as disclosed in U.S. application Ser. No. 11/349,550, filed Feb. 6, 2006, entitled "PCR Elbow Determination by Use of a Double Sigmoid Function Curve Fit with the Levenberg-Marquardt Algorithm and Normalization," which is hereby incorporated by reference in its entirety. Such normalization may be advantageous in the instance where the PCR curve has a significant baseline slope. The cluster analysis processes would then be used after the DSLM with baseline subtraction.

According to another embodiment, outliers (spikes) are removed prior to use of either the DSLM or Cluster Analysis processes. U.S. application Ser. No. 11/316,315, filed Dec. 20, 2005, entitled "Levenberg-Marquardt Outlier Spike Removal Method," discloses useful techniques for removing spikes from a data set. Although both the DSLM and Cluster Analysis processes are somewhat insensitive to outliers, the precision of Ct determination may be increased by performing these methods beforehand.

EXAMPLES

The processes of the present invention are particularly useful in PCR systems, such as thermocyclers, to significantly improve the quality of the PCR results data. Examples of data processed according to the present invention are discussed below.

Figure 8:
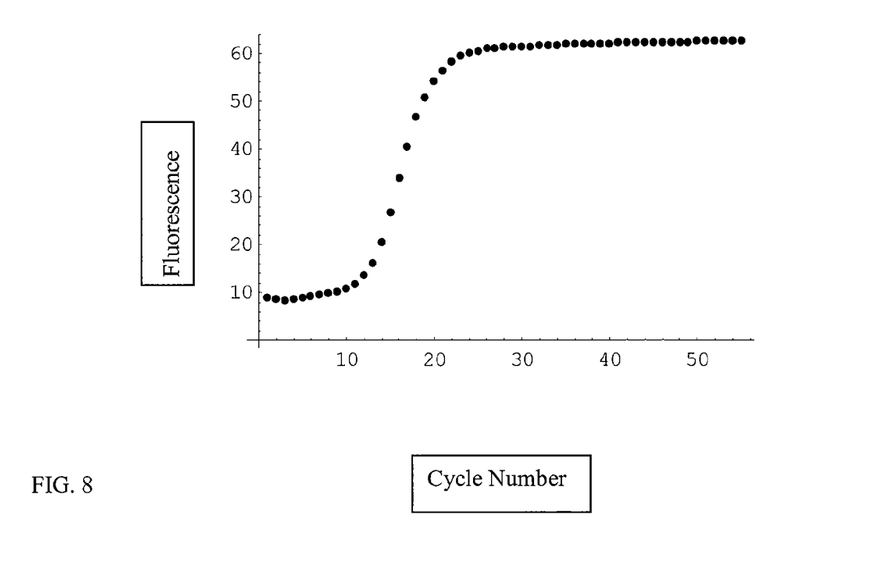
FIG. 8 shows an example of a plotted data set analyzed according to the present invention.

FIG. 8 shows an example of a plotted data set analyzed according to the present invention. This particular data set was difficult to analyze with existing algorithms. When processed through the Cluster Ct Analysis approach of the present invention, the Ct value was determined to be 13.1.

Figure 9:
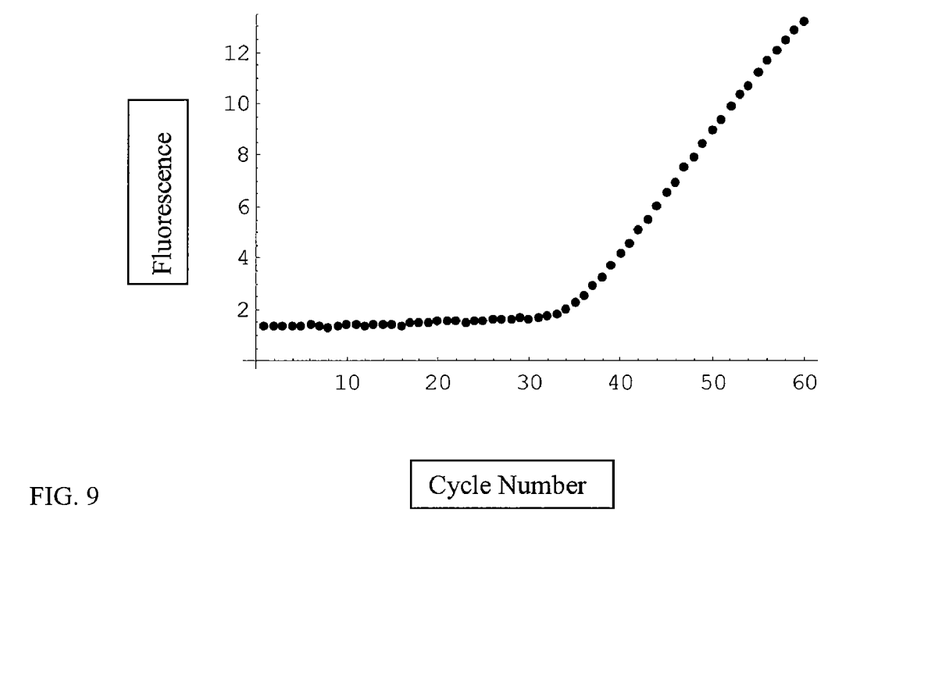
FIG. 9 shows another example of a plotted data set analyzed according to the present invention.

FIG. 9 shows another example of a plotted data set analyzed according to the present invention. This data set, when processed using the Cluster Ct Analysis approach of the present invention, gave the Ct value as 35.9. A traditional approach, which involved normalization, had difficulty with this data set.

Figure 10:
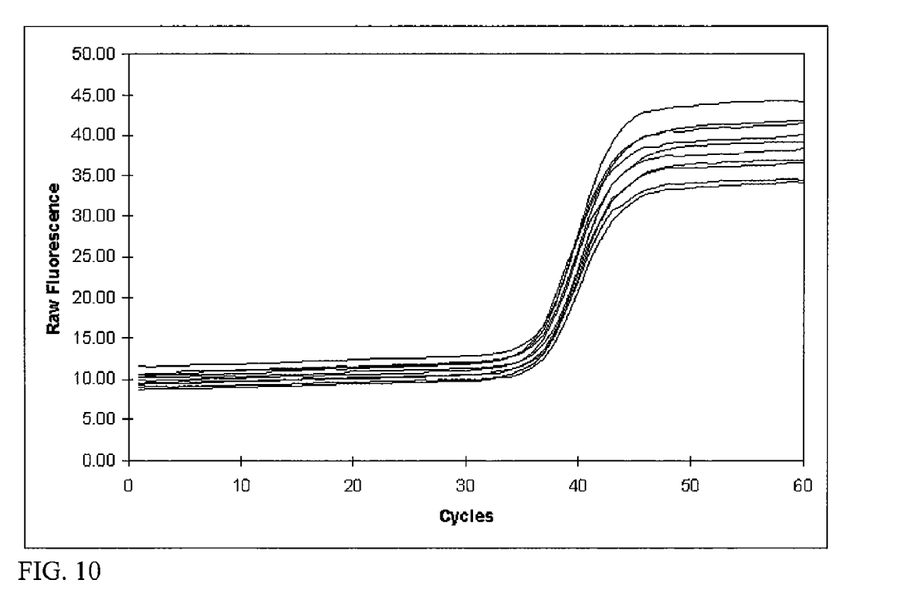
FIG. 10 shows an example of plots of the resultant fluorescence signal from 10 identical samples processed through a thermal cycler and analyzed according to the present invention.

FIG. 10 shows an example of plots of the resultant fluorescence signal from 10 identical samples processed through a thermal cycler and analyzed according to the present invention. The superimposed curves for this data set are shown in FIG. 10. When this data was processed using the cluster approach, the following statistics were obtained:

standard deviation=0.356
mean=35.87
coefficient of variation (Cv)=0.99%

This low value of Cv is excellent.

Figure 11:
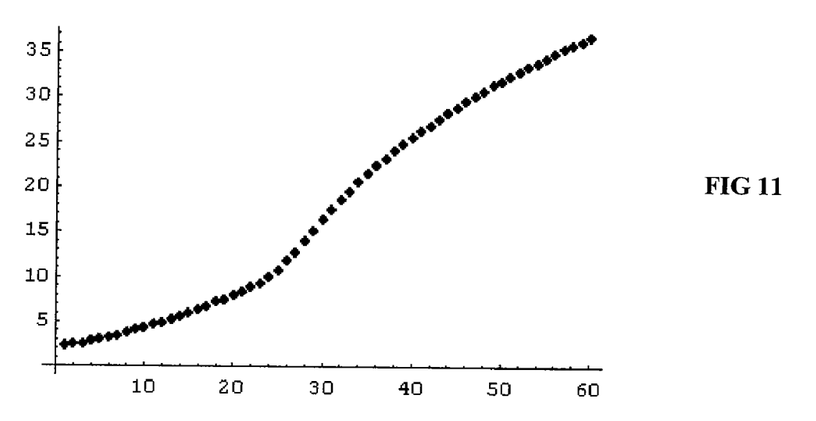
FIG. 11 illustrates a PCR data curve with a high baseline slope.
Figure 12:
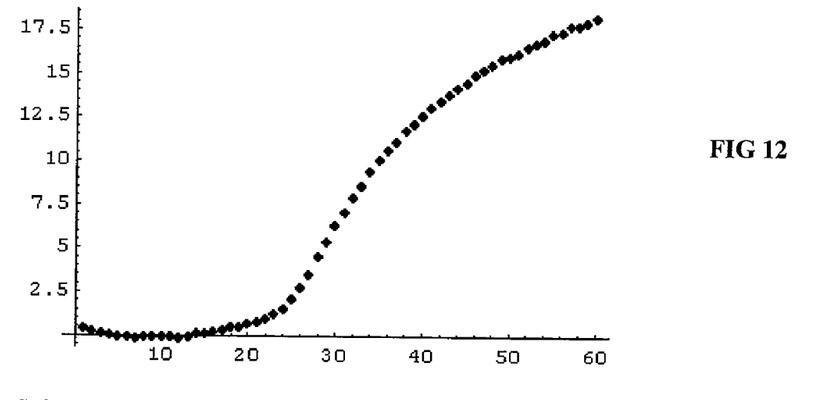
FIG. 12 illustrates the curve of FIG. 11 after correction by baseline subtraction.
Figure 12A:
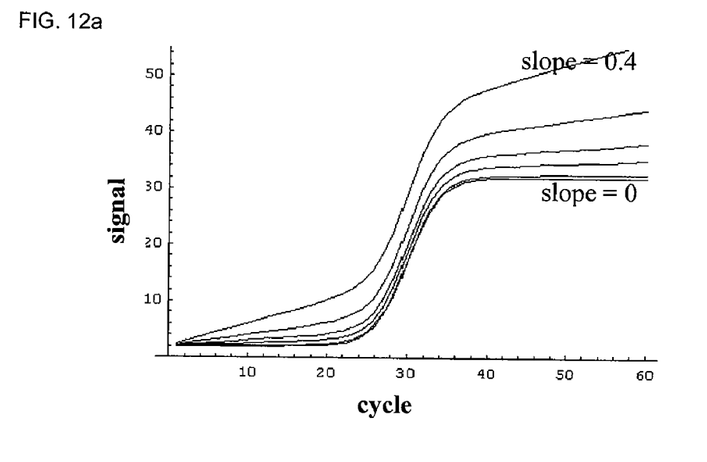
FIG. 12a shows multiple curves to illustrate the influence of baseline slope on Ct determination.
Figure 12B:
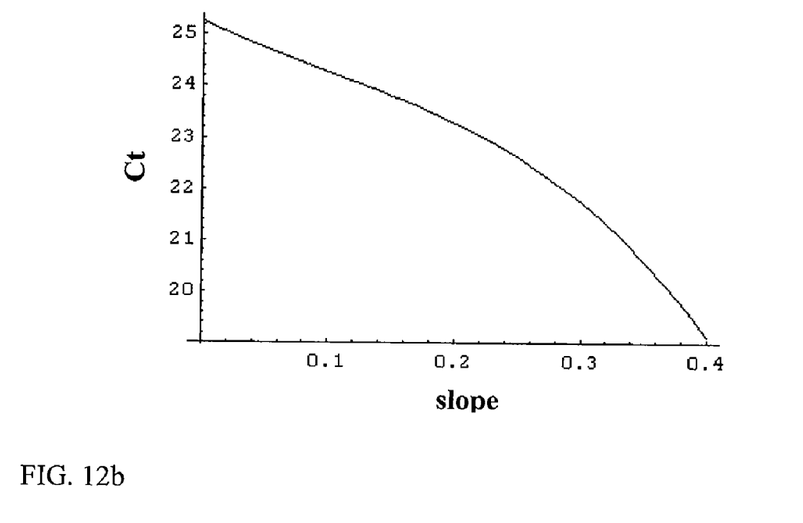

Consider a data set with an extremely high baseline slope as shown in FIG. 11. Upon applying the cluster analysis process to this data set, the Ct value that is returned is Ct=16.5. This value is not correct, however, due to the unusual shape of this curve. If instead, the curve is corrected by baseline subtraction (e.g., using the double sigmoid Levenberg-Marquardt method shown in application Ser. No. 11/394,550), the resultant curve is shown in FIG. 12. The Ct value obtained by the cluster analysis process for this curve is now Ct=24.6, which is much more representative of this baseline normalized data set. The reason that a high baseline slope influences the Ct value determined by cluster analysis is shown in FIG. 12a. The curves are for a theoretically determined sigmoid function, where the only change is the value of the baseline slope, going from an initial value of 0 to 0.4. The Ct value, for these curves changes from 25.1 to 19.7, as shown in FIG. 12b.

Figure 13:
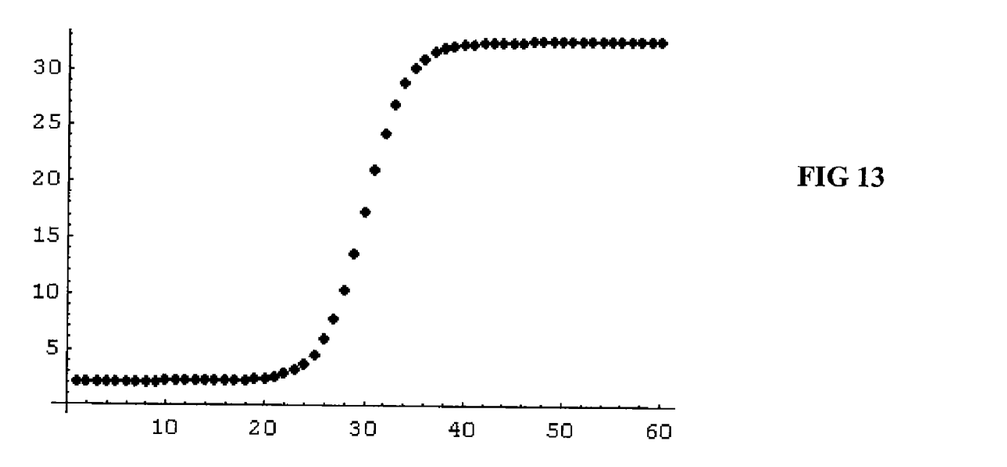
FIG. 13 illustrates a data curve.
Figure 14:
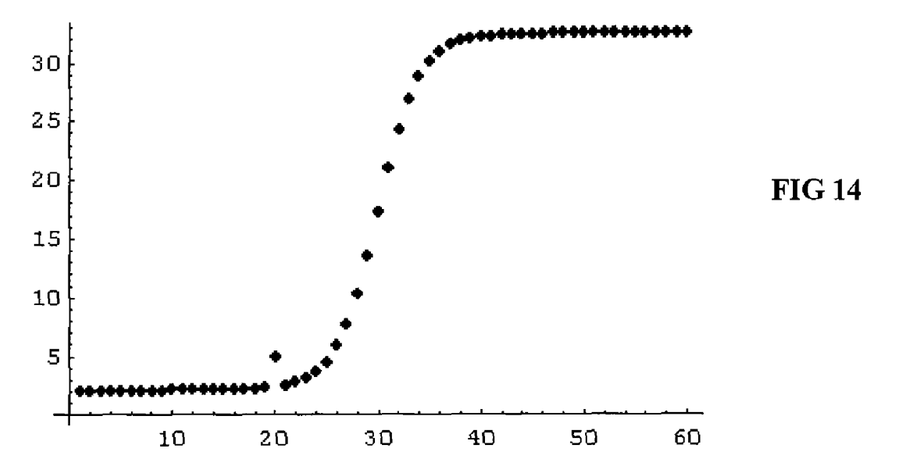
FIG. 14 illustrates the data curve of FIG. 13 with a spike at cycle 20.
Figure 15:
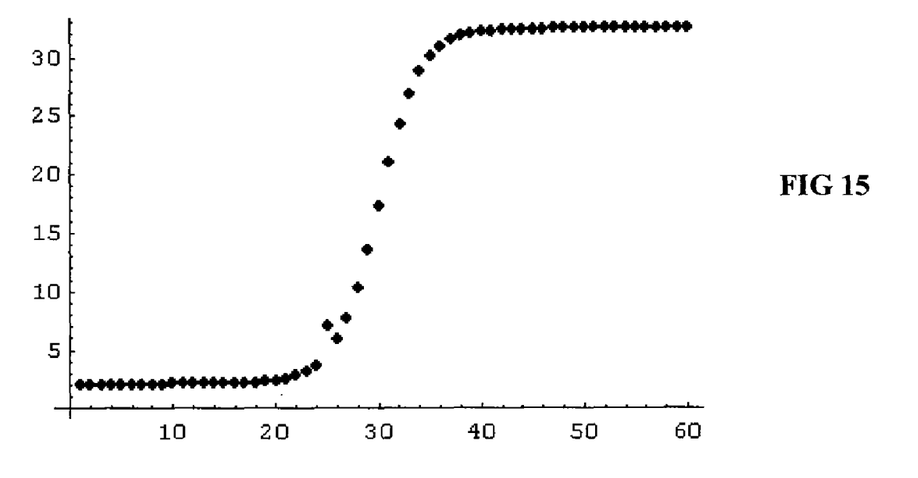
FIG. 15 illustrates the data curve of FIG. 13 with a spike at cycle 25.

Applying the cluster analysis processes to the data set shown in FIG. 13 produces a Ct value of Ct=25.1, which is correct. If a spike is place at cycle number 20, the resultant data set is shown in FIG. 14. Even in the presence of this spike, the Ct value calculated by the cluster analysis processes is still Ct=25.1. This shows the robustness of cluster analysis. If, however, the spike occurs at the Ct value (spike inserted at cycle 25), the resultant plot is shown in FIG. 15. In this case, the Ct is calculated incorrectly, as Ct=23.4. It is therefore highly desirable to remove such spikes before applying cluster analysis. If the data set shown in FIG. 15 is passed through the Levenberg-Marquardt Outlier Method (LMOM) as shown in application Ser. No. 11/313,315, this spike is removed, and the resultant data set is the same as shown in FIG. 13, and the Ct is appropriately calculated as Ct=25.1.

Figure 16:
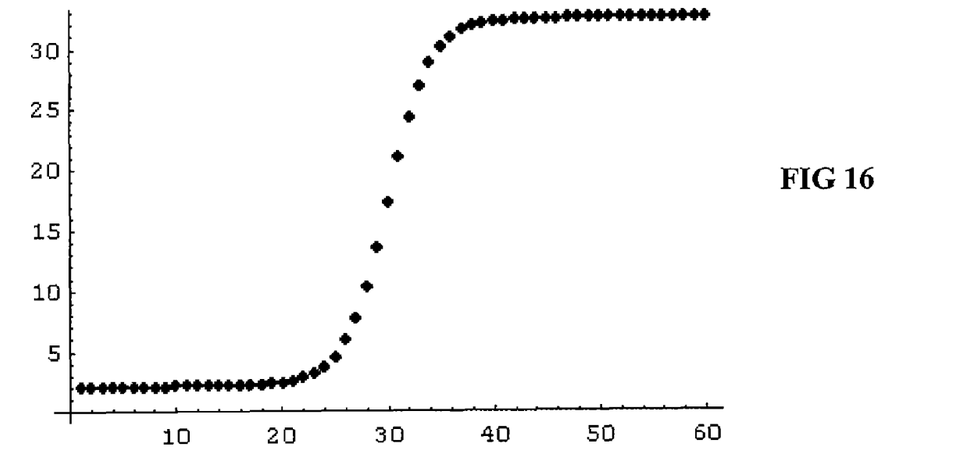
FIG. 16 illustrates a linear interpolated data set.

The Ct value calculated for this data set (FIG. 16) using linear interpolation at 0.1 increments between data points gives Ct=25.1. If instead, the functional form of the Double Sigmoid Levenberg-Marquardt (DSLM) were used at 0.1 increment, then the calculated Ct is Ct=25.0. Although the difference in Ct values in this case is minor, there will be situations where the curvature of the data points is such that the DSLM method is significantly better than linear interpolation.

Figure 17:
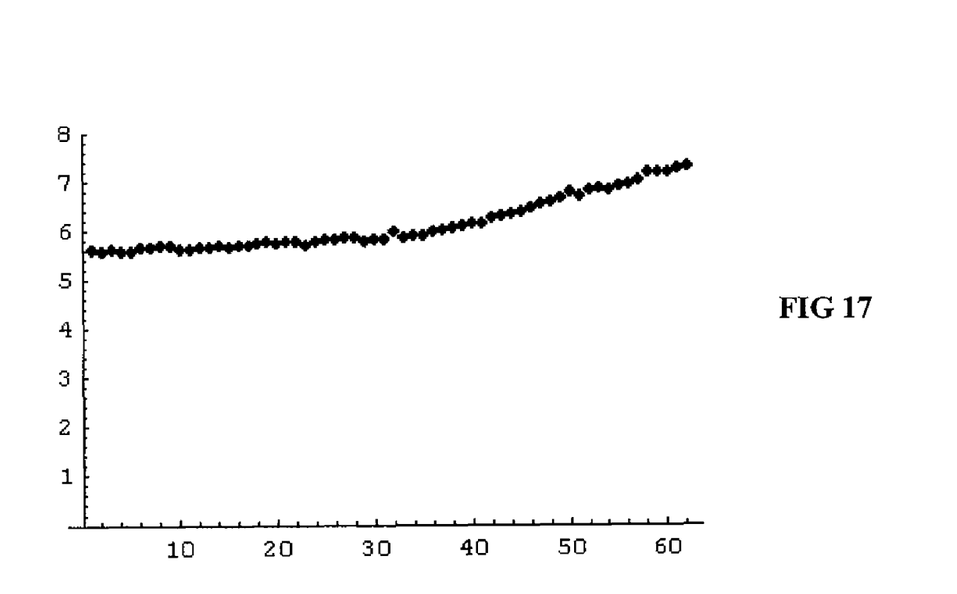
FIG. 17 illustrates a data set that can be classified as representing a "slow grower".

The data set shown in FIG. 17 is classified as a "slow grower", as the increase in the fluorescent signal over the baseline value is small, and the data does not have the classical sigmoid type shape. Using the cluster analysis, the Ct is calculated as Ct=22.9, which does not appear correct. If instead, the variable cluster endpoint method is used, the Ct is calculated as Ct=37.3, which is correct. The slope ratios for this case are: {2.05, 3.065, 0.895, 1.28}, so the Ct corresponds to the endpoint of cluster 2. The RFI and AFI values calculated using the procedure outlined above are 1.26, 1.48 respectively.

CONCLUSION

One skilled in the art should appreciate that the processes of the present invention can be coded using a variety of programming languages such as C, C++, C#, Fortran, VisualBasic, etc., as well as applications similar to Mathematica which may provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, throughout the document, the data set is described with reference to a 2D visual graph system. However, it should be appreciated that a data set may be processed and visualized in any n-dimensional space. For example, the data may be visualized or plotted in a 3D system (e.g., with some arbitrary third dimensional coordinate), and then the cluster analysis transforms performed on any set of two or more coordinate values as desired. Therefore, the scope of the appended claims should be accorded the broadest interpretation so as to encompass all such modifications and similar arrangements.

What is claimed is:

1. A computer-implemented method of determining a specific point of interest in a region of a data curve, the method comprising steps, all steps implemented in a computer system, of:
   receiving a data set representing a data curve, said data set including a plurality of first data points, each first data point having a pair of coordinate values (x,y), wherein if viewed in a two-dimensional coordinate system the data set has a region of interest;
   applying a transformation to at least a portion of the data set including the region of interest to produce a transformed data set, wherein the transformed data set includes a plurality of second data points, each second data point having a pair of coordinate values (y',y*), where the y' coordinate value of a second data point is the y coordinate value of a corresponding first data point, and the y* coordinate value of said second data point is the y coordinate value of a subsequent first data point;
   identifying a plurality of clusters of second data points in the transformed data set;
   determining a linear slope of each of said clusters;
   determining, for each cluster, a ratio of the slope of that cluster with the slope of an adjacent cluster; and
   comparing the ratios;
   wherein an end point of a cluster having the largest or smallest ratio represents a specific point of interest in the data curve.

2. The method of claim 1, wherein the data curve is a curve for a kinetic Polymerase Chain Reaction (PCR) process, and wherein the specific point of interest represents the elbow or cycle threshold (Ct) value for the kinetic PCR curve.

3. The method of claim 2, wherein the first pair of coordinate values represent cycle number and an accumulation of amplified polynucleotide.

4. The method of claim 3, wherein the accumulation of amplified polynucleotide is represented by one of a fluorescence intensity value, a luminescence intensity value, a chemiluminescence intensity value, a phosphorescence intensity value, a charge transfer intensity value, a bioluminescence intensity value, or an absorbance value.

5. The method of claim 1, further including, prior to applying the transformation, interpolating additional first data points using at least the first data points in the region of interest.

6. The method of claim 5, wherein interpolating is performed using one of a linear interpolation process, a cubic spline process, a Levenberg-Marquardt regression process or a least squares fit process.

7. The method of claim 5, wherein interpolating is performed to produce first data points at an incremental scale of about 1.0 or less per coordinate interval along one of said coordinates.

8. The method of claim 7, wherein the incremental scale is about 0.1.

9. The method of claim 5, wherein interpolating includes calculating an approximation of a curve that fits the dataset by applying a Levenberg-Marquardt (LM) regression process to a double sigmoid function to determine parameters of the function.

10. The method of claim 1, wherein the plurality of clusters includes 3 or more clusters.

11. The method of claim 1, wherein identifying clusters includes applying a k-means clustering algorithm to the transformed data set, wherein k is greater than or equal to 3.

12. The method of claim 1, wherein identifying clusters includes applying a Partitioning Around Medoids (PAM) algorithm to the transformed data set to identify 3 or more clusters.

13. The method of claim 10, further including determining whether the data set shows a trend or represents substantially noise data.

14. The method of claim 13, wherein determining whether the data set shows a trend or represents substantially noise data includes calculating a correlation coefficient for each of the clusters, wherein if the correlation coefficient is less than about 0.1 for each cluster, the data is substantially noise.

15. The method of claim 13, wherein determining whether the data set shows a trend or represents substantially noise data includes calculating the endpoint value of each cluster and determining whether each endpoint is less than or greater than the next endpoint value.

16. The method of claim 13, wherein determining whether the data set shows a trend or represents substantially noise data includes calculating a correlation coefficient for the data set, wherein if the correlation coefficient is greater than about 0.99, the data is substantially linear.

17. The method of claim 1, further including calculating a relative fluorescence increase (RFI) value of the data curve by:
calculating a mean value of the last cluster;
calculating a mean value of the first cluster; and
dividing the mean value of the last cluster by the mean value of the first cluster.

18. The method of claim 1, further including calculating an absolute fluorescence increase (AFI) value of the data curve by:
calculating a mean value of the last cluster;
calculating a mean value of the first cluster; and
subtracting the mean value of the first cluster from the mean value of the last cluster.

19. The method of claim 1, further comprising displaying one or both of said data set and said transformed data set in a two dimensional coordinate system on a display device.

20. The method of claim 1, further comprising displaying the y' coordinate value of the specific point of interest on a display device.

21. The method of claim 1, wherein the data curve represents a curve for one of a kinetic Polymarase Chain Reaction (PCR) process, a bacterial process, an enzymatic process or a binding process.

22. The method of claim 1, wherein the data curve is one of a sigmoid type curve or a growth curve.

23. The method of claim 1, wherein the end point is the last point of the cluster.

24. The method of claim 1, wherein the subsequent first data point is the next data point in a contiguous series of data points.

25. The method of claim 1, wherein the subsequent first data point is not the next data point in a contiguous series of data points.

26. The method of claim 1, wherein in the step of determining a ratio of the slope of a cluster, the adjacent cluster is a subsequent cluster, and wherein an end point of the cluster having the smallest ratio represents the specific point of interest.

27. The method of claim 1, wherein in the step of determining a ratio of the slope of a cluster, the adjacent cluster is a previous cluster, and wherein an end point of the cluster having the largest ratio represents the specific point of interest.

28. A non-transitory computer-readable medium that stores code for controlling a processor to determine a cycle threshold (Ct) value in a kinetic Polymerase Chain Reaction (PCR) amplification curve, the code including instructions to:
receive a data set representing a data curve, said data set including a plurality of first data points, each first data point having a pair of coordinate values (x,y), wherein if viewed in a two-dimensional coordinate system the data set has a region of interest;
apply a transformation to at least a portion of the data set including the region of interest to produce a transformed data set, wherein the transformed data set includes a plurality of second data points, each second data point having a pair of coordinate values (y',y*), where the y' coordinate value of a second data point is the y coordinate value of a corresponding first data point, and the y* coordinate value of said second data point is the y coordinate value of a subsequent first data point;
identify a plurality of clusters of second data points in the transformed data set;
determine a linear slope of each of said clusters;
determine, for each cluster, a ratio of the slope of that cluster with the slope of an adjacent cluster; and
compare the ratios;
wherein an end point of a cluster having the largest or smallest ratio represents a specific point of interest in the data curve.

29. A kinetic Polymerase Chain Reaction (PCR) system, comprising:
a kinetic PCR analysis module that generates a PCR data set representing a kinetic PCR amplification curve, said PCR data set including a plurality of first data points each having a pair of coordinate values (x,y), wherein said data set includes data points in a region of interest which includes a cycle threshold (Ct) value; and
an intelligence module adapted to process the PCR data set to determine the Ct value by:
applying a transformation to at least the portion of the PCR data set including the region of interest to produce a transformed data set, wherein the transformed data set includes a plurality of second data points, each second data point having a pair of coordinate values (y',y*), where the y' coordinate value of a second data point is the y coordinate value of a corresponding first data point, and the y* coordinate value of said second data point is the y coordinate value of a subsequent first data point; and
identifying a plurality of clusters of second data points in the transformed data set;
determining a linear slope of each of said clusters;
determining, for each cluster, a ratio of the slope of that cluster with the slope of an adjacent cluster; and
comparing the ratios;
wherein an end point of a cluster having the largest or smallest ratio represents the Ct value in the PCR amplification curve.

30. The method of claim 1, further including:
determining a linear growth portion of the data set; and
normalizing the data set by subtracting off the linear growth portion from the dataset.

* * * * *